United States Patent [19]

Ofuchi et al.

[11] 4,427,670

[45] * Jan. 24, 1984

[54] SKIN PREPARATION

[75] Inventors: Kunihiko Ofuchi, Yokohama; Koichiro Oda, Tokyo; Kenichiro Nakao, Yokohama, all of Japan

[73] Assignee: Mitsubishi Chemical Industries Limited, Tokyo, Japan

[*] Notice: The portion of the term of this patent subsequent to Jun. 8, 1997 has been disclaimed.

[21] Appl. No.: 347,557

[22] Filed: Feb. 10, 1982

Related U.S. Application Data

[63] Continuation-in-part of Ser. No. 243,430, Mar. 13, 1981, Pat. No. 4,333,927.

[30] Foreign Application Priority Data

Mar. 27, 1980 [JP] Japan .................................. 55-39450

[51] Int. Cl.$^3$ ...................... A61K 31/58; A61K 31/56
[52] U.S. Cl. ..................................... 424/241; 424/243

[58] Field of Search ........................ 424/238, 243, 241

[56] References Cited

U.S. PATENT DOCUMENTS 4,282,216 8/1981 Rovee et al. .......................... 424/240
4,333,927 6/1982 Ofuchi et al. ........................ 424/238
4,340,594 7/1982 Mizushima et al. ................. 424/238

Primary Examiner—Elbert L. Roberts
Attorney, Agent, or Firm—Oblon, Fisher, Spivak, McClelland & Maier

[57] ABSTRACT

Skin preparations containing a phosphatide, a topical corticosteroid, and butylhydroxyanisole and/or butylhydroxytoluene, which may be in the form of an aqueous or oily mixture, non-aqueous, water-soluble base or suspension base. These preparations can be applied to various skin diseases including eczema, lichen, ichthyosis and psoriasis, possess improved therapeutic activities and are stable for a prolonged period of time.

1 Claim, No Drawings

SKIN PREPARATION

CROSS-REFERENCE TO RELATED APPLICATIONS

This application is a continuation-in-part of application Ser. No. 243,430 filed Mar. 13, 1981. now U.S. Pat. No. 4,333,927.

BACKGROUND OF THE INVENTION

This invention relates to a skin preparation and more particularly to a skin preparation exerting an improved therapeutic activity of a topical corticosteroid present therein.

Topical corticosteroid-containing skin preparations have heretofore been used widely. However, it is still desired to improve the efficacy of these skin preparations.

SUMMARY OF THE INVENTION

It is an object of this invention to provide a topical corticosteroid-containing skin preparation having an enhanced therapeutic activity.

Other objects will be apparent from the following description.

We have now found that these objects can be attained by incorporating a phosphatide and butylhydroxyanisole and/or butylhydroxytoluene in the skin preparation and accomplished this invention.

In brief, this invention resides in a skin preparation which contains (i) a phosphatide, (ii) a topical corticosteroid and (iii) butylhydroxyanisole and/or butylhydroxytoluene.

DETAILED DESCRIPTION OF PREFERRED EMBODIMENTS

The phosphatides which can be used in the skin preparations of this invention include phosphatidylcholine (lecithin), phosphatidylethanolamine (cephlin), phosphatidylserine, phosphatidylinositol, phosphatidic acid and the like. Of course, a mixture of two or more of these phosphatides may be used. In such cases, it was found that the phosphatidylcholine content of the phosphatide mixture is most preferably between 10% and 40%. This is presumed to have relation to the fact that such phosphatidylcholine content is close to the phosphatide composition of the epidermis. It is generally advantageous to use as the phosphatide mixture a commercially available soy phosphatide (soy lecithin) or egg phosphatide (egg lecithin). Soy phosphatide is particularly preferred. These commercially available phosphatides contain various phosphatides and in addition some substances other than phosphatides. The amount of such commercially available phosphatide to be used should be calculated based on the total phosphatide content thereof. The amount of phosphatides or phosphatide mixture used in the skin preparation of this invention depends on the diseases to which the skin preparation is applied, formulation, type and amount of the topical corticosteroid and the like, and is usually in the range of 0.1% to 30%, preferably 0.1% to 10%, more preferably 0.2% to 7% and most preferably 0.5 to 5% by weight based on the total weight of the preparation.

If the amount of phosphatide used is too low, the desired results of this invention will be attained insufficiently. The use of more phosphatide than required will not improve the desired results in a manner proportional to the amount of phosphatide, and bring about undesirable effects such as stickiness of the skin. For this reason, the above-mentioned range is preferred.

Examples of the topical corticosteroid for use in the skin preparations of this invention include hydrocortisone acetate, hydrocortisone butyrate, prednisolone acetate, methylprednisolone acetate, dexamethasone acetate, dexamethasone sodiumphosphate, dexamethasone valerate, flumethasone pivalate, beclomethasone dipropionate, betamethasone valerate, betamethasone dipropionate, betamethasone sodiumphosphate, betamethasone benzoate, fluocinolone acetonide, clobetasone, butyrate, clobetasol propionate, diflucortolone valerate, diflucortolone pivalate, flucortin butyl, fluocortolone, clocortolone pivalate, halcinonide, amcinonide, diflorasone diacetate, desoxymethasone, difluprednate, desonide, budesonide, prednisone, paramethasone, fludroxycortide and flunisolide. Of course, a combination of two or more of these topical corticosteroids may be used.

The amount of the topical corticosteroid to be added should be determined on the basis of the strength of activity and the intended use of the particular corticosteroid. When a larger amount of the topical corticosteroid is added, it is preferred to increase the amount of the phosphatide added. In preparing the skin preparation of this invention, the topical corticosteroid can be added as a solution dissolved in an oil phase component, or propylene glycol, polyethylene glycol, ethanol or the like. Alternatively, solid powder of the corticosteroid may be added and dispersed as such or after it is finely pulverized.

The skin preparation of this invention contains butylhydroxyanisole and/or butylhydroxytoluene along with the aforementioned phosphatide and topical corticosteroid.

The incorporation of butylhydroxyanisole and/or butylhydroxytoluene prevents very satisfactorily the phosphatide from coloring and keeps the skin preparation very stable for a prolonged period of time. Particularly, a combined use of both these compounds provides satisfactory results.

In the preparation of an ointment, predissolution of the topical corticosteroid in propylene glycol is preferred in view of solubility and mild irritation to the skin, but this suffers from instability with elapse of time. In such cases, a highly stable ointment can be obtained by dissolving the corticosteroid in propylene glycol in which butylhydroxyanisole has been dissolved, because butylhydroxyanisole in soluble in propylene glycol.

In addition to the above-mentioned three components, other components may be incorporated in the skin preparation of this invention depending on the intended use thereof. Thus, it is possible to prepare skin preparations having a wide variety of rheological properties in a conventional manner. The formulations of these skin preparations include aqueous mixtures such as a solution, colloidal solution, emulsified lotion, O/W cream (hydrophilic cream) and aqueous gel wherein the aqueous phase is the continuous one; oily mixtures such as a solution, ointment, W/O cream, gel base [e.g. Plastibase ® (a mineral oil gelled with polyethylene, i.e., a gel of polyethylene and liquid paraffin)], absorption ointment in which an emulsifier is added to the oil and hydrophilic ointment wherein the oil phase is the continuous one; and non-aqueous, water-soluble bases such as a mixture of polyethylene glycol. A suspension base such as a shaking lotion in which a solid dispersing agent is added can also be prepared.

Oily components, emulsifiers, dispersing agents, gelatinizers and solid materials which can be used to prepare such formulations are well known as those used in the preparation of cosmetics and topical products.

The oily components include hydrocarbons such as liquid paraffin, vaseline, solid paraffin, microcrystalline wax, etc.; higher aliphatic alcohols such as cetyl alcohol, hexadecyl alcohol, stearyl alcohol, oleyl alcohol, etc.; esters of higher fatty acids with higher alcohols such as beeswax, spermaceti, etc.; esters or higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like.

Emulsifiers and dispersing agents which can be used include anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate; etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

Particularly in the preparation of creams, the use of a polyoxyethylene fatty acid ester is advantageous in that the emulsion stability is highly improved. Particularly preferred for this purpose are those polyoxyethylene fatty acid esters wherein the fatty acid contains usually about 8 to 26 carbon atoms, preferably about 12 to 18 carbon atoms and the number of ethylene oxide molecules in the addition polymerized polymer chains (or degree of addition polymerization of ethylene oxide) is usually about 20 to 60, preferably about 40 to 55. An example of such ester is polyoxyethylene monostearate.

Gelatinizers include carboxymethylcellulose, cellulose gel, carbopol, polyvinyl alcohol, polyethylene glycol and various gums.

These oily components, emulsifiers, dispersing agents and gelatinizers, of course, can be used alone or in combination with each other.

The incorporation into the skin preparation of this invention of propylene glycol, glycerine, sorbitol or the like which has a moisturizing action is preferred, because it enhances the moisturizing action of the skin preparation of this invention. Ethanol may be added to advantage, since it has a bacteriostatic action and provides a cooling effect upon application to the skin.

In order to further increase the stability of the skin preparation of this invention it is preferred to add a chelating agent, an antiseptics and the like, as required. The chelating agents which can be used include EDTA (ethylenediamine tetracetate), thioglycolic acid, thiolactic acid, thioglycerine and the like. The antiseptics which can be used include methyl, ethyl, propyl and butyl esters of p-hydroxybenzoic acid, o-phenylphenol, dehydroacetic acid and the salts thereof, p-chloro-m-cresol, p-chloro-m-xylenol and the like.

In addition, it is preferred to adjust pH of the skin preparation by adding citric acid, lactic acid, tartaric acid or the like. The pH value which should be adjusted to is dependent upon the stability of the skin preparation. In general, it is preferred that the skin preparation be slightly acidic to slightly alkaline. A fragrance may be added in a slight amount, if desired.

Furthermore, one or more drugs selected from antibiotics, antihistaminics, antimycotic agents and vitamines may be incorporated into the skin preparation of this invention to prepare a compounded preparation.

Since the skin preparations according to this invention exerts a markedly improved activity of the topical corticosteroid present therein, they can be used in the treatment of skin diseases including eczema, ichthyosis, lichen and psoriasis to attain the disappearance or alleviation of the sympton.

In addition, the skin preparations of this invention disperse and retain the active ingredient, corticosteroid, in the skin for a prolonged period of time without loss of the corticosteroid so that they can exert the effect of the steroid effectively.

Furthermore, the skin preparations are stable with little coloration or other change after the elapse of time.

The following examples are given to illustrate this invention, but they are not intended to restrict the invention in any way.

EXAMPLES 1 TO 6 AND COMPARATIVE EXAMPLES A TO D

Various topical corticosteroid-containing skin preparations having the compositions given in Table 1 below were prepared.

TABLE 1

| | Example 1 | Example 2 | Comparative A | Example 3 | Example 4 | Comparative B | Example 5 | Comparative C | Example 6 | Comparative D |
|---|---|---|---|---|---|---|---|---|---|---|
| Formulation | Oleagenous anhydrous ointment | Oleagenous anhydrous ointment | Oleagenous anhydrous ointment | O/W cream | O/W cream | O/W cream | Oleagenous anhydrous ointment | Oleagenous anhydrous ointment | O/W cream | O/W cream |
| Composition | % | % | % | % | % | % | % | % | % | % |
| Fluocinolone acetonide | 0.025 | 0.025 | 0.025 | 0.025 | 0.025 | 0.025 | — | — | — | — |
| Hydrocortisone acetate | — | — | — | — | 13 | — | 1.0 | 1.0 | 1.0 | 1.0 |
| Soy phosphatide | 4.0 | 2.0 | — | 4.0 | 2.0 | — | 4.0 | — | 4.0 | — |
| White petrolatum | — | 87.945 | — | 9.9 | 9.9 | 9.9 | 89.975 | 93.975 | 9.9 | 9.9 |
| Liquid paraffin | — | 5.0 | — | 12.9 | 12.9 | 12.9 | 5.0 | 5.0 | 12.9 | 12.9 |
| Plastibase ® 50W | 95.95 | — | 99.95 | — | — | — | — | — | — | — |
| Butylated hydroxytoluene | 0.025 | 0.025 | 0.025 | 0.025 | 0.05 | 0.025 | 0.025 | 0.025 | 0.025 | 0.025 |
| Butylated hydroxyanisole | — | 0.005 | — | — | — | — | — | — | — | — |
| Stearyl alcohol | — | — | — | 5.0 | 2.1 | 5.0 | — | — | 5.0 | 5.0 |
| Cetyl alcohol | — | — | — | 2.1 | 5.0 | 2.1 | — | — | 2.1 | 2.1 |
| Polyoxyethylene cetyl ether | — | — | — | 4.0 | — | 1.7 | — | — | 1.7 | 1.7 |
| Polyoxyethylene | — | — | — | — | 4.0 | — | — | — | — | — |

TABLE 1-continued

| Composition | Example 1 | Example 2 | Comparative A | Example 3 | Example 4 | Comparative B | Example 5 | Comparative C | Example 6 | Comparative D |
|---|---|---|---|---|---|---|---|---|---|---|
| | Oleagenous anhydrous ointment | | | O/W cream | | | Oleagenous anhydrous ointment | | O/W cream | |
| | % | % | % | % | % | % | % | % | % | % |
| monostearate | | | | | | | | | | |
| Ethyl p-hydroxybenzoate | — | — | — | 0.1 | 0.1 | 0.1 | — | — | 0.1 | 0.1 |
| Methyl p-hydroxybenzoate | — | — | — | — | 0.2 | — | — | — | — | — |
| Butyl p-hydroxybenzoate | — | — | — | 0.1 | 0.1 | 0.1 | — | — | 0.1 | 0.1 |
| Propylene glycol | — | 5.0 | — | — | — | — | — | — | — | — |
| Purified water | — | — | — | 61.85 | 63.625 | 68.15 | — | — | 63.175 | 67.175 |
| Total (% by weight) | 100.0 | 100.0 | 100.0 | 100.0 | 100.0 | 100.0 | 100.0 | 100.0 | 100.0 | 100.0 |

The activities of these ten preparations having the compositions as above were evaluated and compared by their antiinflammatory effects on mice croton oil ear edema.

[Test Procedure]

The test was carried out according to the Toneli method [Endocrinology 77, 625–634 (1965)].

A phlogistic solution consisting of pyridine, ether and croton oil [50:45:5 (v/v)] is applied to the right ear of the mouse and then the skin preparation is applied thereon. Five hours after the treatment, both of the ears are excised at a predetermined position and the wet weight of the ears are dtermined to calculate the edema ratio according to the following equation:

$$\text{Edema Ratio (\%)} = \left(\frac{\text{Weight of Right Ear}}{\text{Weight of Left Ear}} - 1\right) \times 100$$

Inhibition ratio is calculated according to the following equation:

$$\text{Inhibition Ratio (\%)} = \left(1 - \frac{\text{Edema ratio when treated with ointment}}{\text{Edema ratio when untreated}}\right) \times 100$$

Ten male mice weighing 20 to 25 g are used as one group.

[Test Results]

As is apparent from Table 2 below, the skin preparations of this invention possess higher antiinflammatory activities as campared with topical corticosteroid preparations prepared with conventional ointment bases.

From these results, it is believed that the increased activities of the skin preparations of this invention result from the formation of a non-covalent complex between the steroid and the phosphatide which leads to an increase in the compatibility and retainability of the steroid in the skin.

TABLE 2

Effects on mouse croton oil ear edema

| Drug | Example No. | Formulation | Edema ratio (%) | Inhibition ratio (%) | Effect* |
|---|---|---|---|---|---|
| Fluocinolone acetonide | Example 1 | Oleagenous anhydrous ointment | 21.8 | 83.6 | +++ |
| | Example 2 | | 24.1 | 81.9 | +++ |
| | Comparative A | | 40.1 | 69.9 | ++ |
| | Example 3 | O/W cream | 30.5 | 77.1 | +++ |
| | Example 4 | | 31.4 | 76.4 | +++ |
| | Comparative B | | 54.8 | 58.9 | ++ |
| Hydrocortisone acetate | Example 5 | Oleagenous anhydrous ointment | 35.6 | 73.3 | +++ |
| | Comparative C | | 52.1 | 60.9 | ++ |
| | Example 6 | O/W cream | 37.0 | 72.2 | +++ |
| | Comparative D | | 53.8 | 59.6 | ++ |
| Untreated | | — | 133.3 | — | — |

| *Score | Inhibition Ratio |
|---|---|
| +++ | 70–100% |
| ++ | 40–70% |
| + | 10–40% |
| ± | 0–10% |

EXAMPLES 7 TO 9 AND COMPARATIVE EXAMPLES E AND F

Topical corticosteroid-containing skin preparations having the compositions given in Table 3 below were prepared.

TABLE 3

| Composition | Example 7 | Comparative E | Example 8 | Example 9 | Comparative F |
|---|---|---|---|---|---|
| | Oleagenous anhydrous ointment | | Absorption ointment | Macrogol ointment | |
| | % | % | % | % | % |
| Densonide | 0.1 | 0.1 | 0.1 | — | — |
| Methylprednisolone acetate | — | — | — | 1.0 | 1.0 |
| Soy phosphatide | 4.0 | — | 4.0 | 4.0 | — |
| White petrolatum | — | — | 40.0 | — | — |
| Liquid paraffin | — | — | — | 10.0 | — |
| Macrogol 4000 | — | — | — | 41.0 | 48.0 |
| Macrogol 400 | — | — | — | 43.95 | 50.975 |
| Plastibase ® 50W | 95.875 | 99.875 | — | — | — |

TABLE 3-continued

|  | Example 7 | Comparative E | Example 8 | Example 9 | Comparative F |
|---|---|---|---|---|---|
|  |  |  | Formulation |  |  |
|  | Oleagenous anhydrous ointment | | Absorption ointment | Macrogol ointment | |
| Composition | % | % | % | % | % |
| Butylated hydroxytoluene | 0.025 | 0.025 | 0.025 | 0.025 | 0.025 |
| Cetyl alcohol | — | — | 18.0 | — | — |
| Sorbitan sesquioleate | — | — | 5.0 | — | — |
| Polyoxyethylene lauryl ether | — | — | 0.5 | — | — |
| Ethyl p-hydroxybenzoate | — | — | 0.1 | — | — |
| Butyl p-hydroxybenzoate | — | — | 0.1 | — | — |
| Purified water | — | — | 32.175 | — | — |
| Total (% by weight) | 100.0 | 100.0 | 100.0 | 100.0 | 100.0 |

The antiinflammatory activities of these five skin preparations were evaluated and compared by rat skin carrageenin edema inhibition test.

[Test Procedure]

The test was carried out according to the Fujimura et al method.

A 1% solution of λ carrageenin dissolved in the Krebs solution is used as a phlogistic solution. On the day before the test, the abdominal hair of the rats is completely removed using a hair clipper and a depilatory cream.

About 0.5 g of the ointment or cream to be tested is applied to the abdominal skin of the rats under no anesthetic. An hour after this treatment, 5.0 µl of the 1% carrageenin solution is injected intradermally at two points of the abdomen under no anesthetic. Immediately after this injection, 0.5 ml of 1% pontamine sky blue solution (in the Krebs solution) is injected through the tail vein, and at the same time 0.5 g of the drug (ointment or cream) is applied to the abdominal skin again. Then, blue areas and edemas on the abdominal skin of the rats are measured every one hour after application of the carrageenin solution. Five hours after the application, the rats are sacrificed by exsanguination and the abdominal skin are excised and reversed to measure the shortest and longest diameters of the blue areas. The edema areas are then punched out with a 17×17 mm skin punch and their wet weights are measured to give indices of the skin edemas.

[Test Results]

It is apparent from Table 4 below that the skin preparations of this invention possess higher carrageenin edema inhibitory activities as compared with the comparative topical corticosteroid preparations prepared with conventional ointment bases.

TABLE 4

| Drug | Example No. | Formulation | Edema[1] Weight (mg) | Inhibition ratio (%) [2] | Edema[3] ratio (%) | Inhibition ratio (%) | Blue area (mm$^2$) | Inhibition ratio (%) | Mean Inhibition ratio (%) | Overall[4] effect |
|---|---|---|---|---|---|---|---|---|---|---|
|  |  |  |  | Effects on Rat Carrageenin Edema | | | | | | |
| Desonide | Example 7 | Oleagenous | 60.8 | 51.4 | 81.1 | 46.2 | 70.8 | 46.1 | 47.9 | ++ |
|  | Comparative E | anhydrous ointment | 75.2 | 39.9 | 100.3 | 33.4 | 82.9 | 36.9 | 36.7 | + |
|  | Example 8 | Absorption ointment | 62.5 | 50.1 | 83.3 | 44.7 | 72.2 | 45.1 | 46.6 | ++ |
| Methylprednisolone acetate | Example 9 | Macrogol ointment | 50.4 | 59.7 | 82.2 | 45.5 | 79.8 | 39.3 | 48.2 | ++ |
|  | Comparative F |  | 60.6 | 51.6 | 98.9 | 34.4 | 88.9 | 32.3 | 39.4 | + |
| Untreated |  | — | 125.7 | — | 150.7 | — | 131.4 | — | — | — |

[1]Edema weight = Edema skin weight − Normal skin weight
[2]Inhibition ratio = (Measured value when treated with ointment − Measured value when untreated) / (Measured value when untreated) × 100
[3]Edema ratio = (Edema skin weight / Normal skin weight) × 100
[4]Overall effect was evaluated from the mean inhibition ratio for the edema weight, edema ratio and blue area when treated with ointment.

| Score | Inhibition ratio |
|---|---|
| ++ | 40–60% |
| + | 20–40% |
| ± | 0–20% |

The soy phosphatide used in the test contained 30 to 32% phosphatidylcholine based on the total phosphatide content of the soy phosphatide.

EXAMPLE 10 AND COMPARATIVE EXAMPLE G

Topical corticosteroid-containing skin preparations having the compositions given in Table 5 below were prepared.

TABLE 5

|  | Example 10 | Comparative G |
|---|---|---|
|  | Formulation | |
|  | Oleagenous anhydrous ointment | |
| Composition | % | % |
| Fludroxycortide | 0.12 | 0.12 |
| Soy phosphatide | 4.0 | — |
| White petrolatum | 78.855 | 82.855 |
| Liquid paraffin | 5.0 | 5.0 |
| Purified lanolin | 4.0 | 4.0 |

TABLE 5-continued

| Composition | Example 10 | Comparative G |
|---|---|---|
| | Formulation | |
| | Oleagenous anhydrous ointment | |
| | % | % |
| Butylated hydroxytoluene | 0.025 | 0.025 |
| Stearyl alcohol | 8.0 | 8.0 |
| Total (% by weight) | 100.0 | 100.0 |

The activities of these two preparations having the above compositions were evaluated and compared by their antiinflammatory effects on rat croton oil ear edema. The test procedure were the same as described in Examples 1 to 4 except that mice were replaced by rats. The results are shown in Table 6 below.

TABLE 6

| | Effects on rat croton oil ear edema | | |
|---|---|---|---|
| Example No. | Edema ratio (%) | Inhibition ratio (%) | Effect* |
| Example 10 | 35.6 | 64.9 | ++ |
| Comparative G | 50.1 | 50.6 | ++ |
| Untreated | 101.4 | — | — |

*The scores are the same as described in Table 2.

As is apparent from Table 6, the skin preparation of this invention possesses a higher antiinflammatory activity as compared with the comparative skin preparation prepared with conventional ointment bases, as evaluated by the rat croton oil ear edema test.

EXAMPLE 11 AND COMPARATIVE EXAMPLE H

Topical corticosteroid-containing skin preparations having the compositions given in Table 7 below were prepared.

TABLE 7

| Composition | Example 11 | Comparative H |
|---|---|---|
| | Formulation | |
| | O/W cream | |
| | % | % |
| Fluocinolone acetonide | 0.025 | 0.025 |
| Soy phosphatide | 2.0 | 2.0 |
| White petrolatum | 9.9 | 9.9 |
| Liquid paraffin | 12.9 | 12.9 |
| Stearyl alcohol | 2.1 | 2.1 |
| Cetyl alcohol | 5.0 | 5.0 |
| Polyoxyethylene monostearate | 4.0 | 4.0 |

TABLE 7-continued

| Composition | Example 11 | Comparative H |
|---|---|---|
| | Formulation | |
| | O/W cream | |
| | % | % |
| Ethyl p-hydroxybenzoate | 0.1 | 0.1 |
| Butyl p-hydroxybenzoate | 0.1 | 0.1 |
| Butylated hydroxytoluene | 0.025 | — |
| Purified water | 63.85 | 63.75 |
| Total (% by weight) | 100.0 | 100.0 |

The preparation of Example 11 contained butylated hydroxytoluene, while that of Comparative Example H was free from the same.

In order to compare the stability with elapse of time, the two preparations having the compositions as above were each packed into a JIS No. 6 glass bottle and kept in a thermostat at 40° C. for 12 weeks, during which the change in appearance was observed. The results are summarized in Table 8.

TABLE 8

| Example No. | Item observed | Storage period at 40° C. | | | |
|---|---|---|---|---|---|
| | | 1 week | 4 weeks | 8 weeks | 12 weeks |
| Example 11 | Surface coloration | — | — | — | — |
| | Separation | — | — | — | — |
| Comparative H | Surface coloration | — | + | ++ | ++ |
| | Separation | — | — | ± | ± |
| Score | | | | | |
| ++ | | Significant change | | | |
| + | | Change | | | |
| ± | | Indistinct change | | | |
| — | | No change | | | |

It can be seen from Table 8 that the skin preparation of this invention possesses a significantly improved storage stability, particularly with respect to surface coloration, as compared with that of the preparation of Comparative Example H which is free from butylated hydroxytoluene.

What is claimed is:

1. A skin preparation containing at least one topical corticosteroid selected from the group consisting of diflucortolone valerate, diflucortolone pivalate, flucortin butyl, fluocortolone, clocortolone pivalate, halcinonide, amcinonide, diflorasone diacetate, desoxymethasone, difluprednate, desonide, budesonide, prednisone, paramethasone, fludroxycortide and flunisolide, and an effective amount of a phosphatide and at least one of butylhydroxyanisole and butylhydroxytoluene to impart stability to the preparation for a prolonged period.

* * * * *